United States Patent [19]
Lawson et al.

[11] Patent Number: 6,046,288
[45] Date of Patent: *Apr. 4, 2000

[54] METHOD OF PREPARING A POLYMER USING ALIPHATIC SOLUTIONS OF AMINOALKYLLITHIUM COMPOUNDS

[75] Inventors: David F. Lawson, Uniontown; Michael L. Kerns, Elyria; John R. Schreffler, Clinton, all of Ohio

[73] Assignee: Bridgestone Corporation, Tokyo, Japan

[*] Notice: This patent is subject to a terminal disclaimer.

[21] Appl. No.: 08/936,253

[22] Filed: Sep. 24, 1997

Related U.S. Application Data

[63] Continuation of application No. 08/904,497, Aug. 1, 1997, Pat. No. 5,935,893.

[51] Int. Cl.$^7$ .............................. C08F 36/04; C08F 4/48
[52] U.S. Cl. ..................... 526/175; 526/180; 526/181; 526/217; 526/220; 526/335; 526/340; 525/370; 525/371
[58] Field of Search ..................... 526/180, 181, 526/335, 175, 217, 220; 524/571, 370; 525/370, 371

[56] References Cited

U.S. PATENT DOCUMENTS

| | | | |
|---|---|---|---|
| 2,849,432 | 8/1958 | Kibler et al. | 526/180 |
| 3,290,277 | 12/1966 | Anderson et al. | 526/180 X |
| 4,935,471 | 6/1990 | Halasa | 525/359.1 |
| 5,149,457 | 9/1992 | Smith | 252/182.12 |
| 5,173,209 | 12/1992 | Smith, Jr. et al. | 525/182.14 |
| 5,329,005 | 7/1994 | Lawson et al. | 540/450 |
| 5,332,810 | 7/1994 | Lawson | 540/450 |
| 5,496,940 | 3/1996 | Lawson | 540/450 |
| 5,550,203 | 8/1996 | Engel et al. | 526/336 |
| 5,552,473 | 9/1996 | Lawson et al. | 524/575 |
| 5,574,109 | 11/1996 | Lawson | 525/280 |
| 5,578,542 | 11/1996 | Lawson et al. | 502/167 |
| 5,616,704 | 4/1997 | Lawson et al. | 540/450 |
| 5,643,848 | 6/1997 | Lawson et al. | 502/167 |
| 5,723,533 | 3/1998 | Lawson et al. | 526/180 X |
| 5,785,778 | 7/1998 | Lawson et al. | 526/180 X |
| 5,935,893 | 8/1999 | Lawson et al. | 502/157 |

FOREIGN PATENT DOCUMENTS 316 255 A2  10/1988  European Pat. Off. .

OTHER PUBLICATIONS

Organic Solvents (3$^{rd}$ Edition) Wiley–Interscience, NY, pp. 52–53, 1970, by Riddick et al.
*Eur. Polym. J.*, 1975, 11, p. 699, by Eisenbach et al.
*J. Polym. Sci., Polym. Chem. Edition*, 1983, 21, p. 2237, by Worlsford.
*Br. Polym. J.*, 1990, 22, pp. 319–325, by Stewart et al.
*Polymer*, 1995, 36, p. 3005, by Pispas et al.
Hackh's Chem. Dictionary (4th edition) Mc–Graw–Hill, N.Y., p. 25, 27, 1969.

*Primary Examiner*—Fred Teskin
*Attorney, Agent, or Firm*—John H. Hornickel; Daniel N. Hall; Arthur M. Reginelli

[57] ABSTRACT

A method for reducing the amount of aliphatic solvent needed for maintaining aminoalkyllithium initiators in solution comprising the step of combining at least one aminoalkyllithium compound with a second, dissimilar lithioamine.

12 Claims, 1 Drawing Sheet

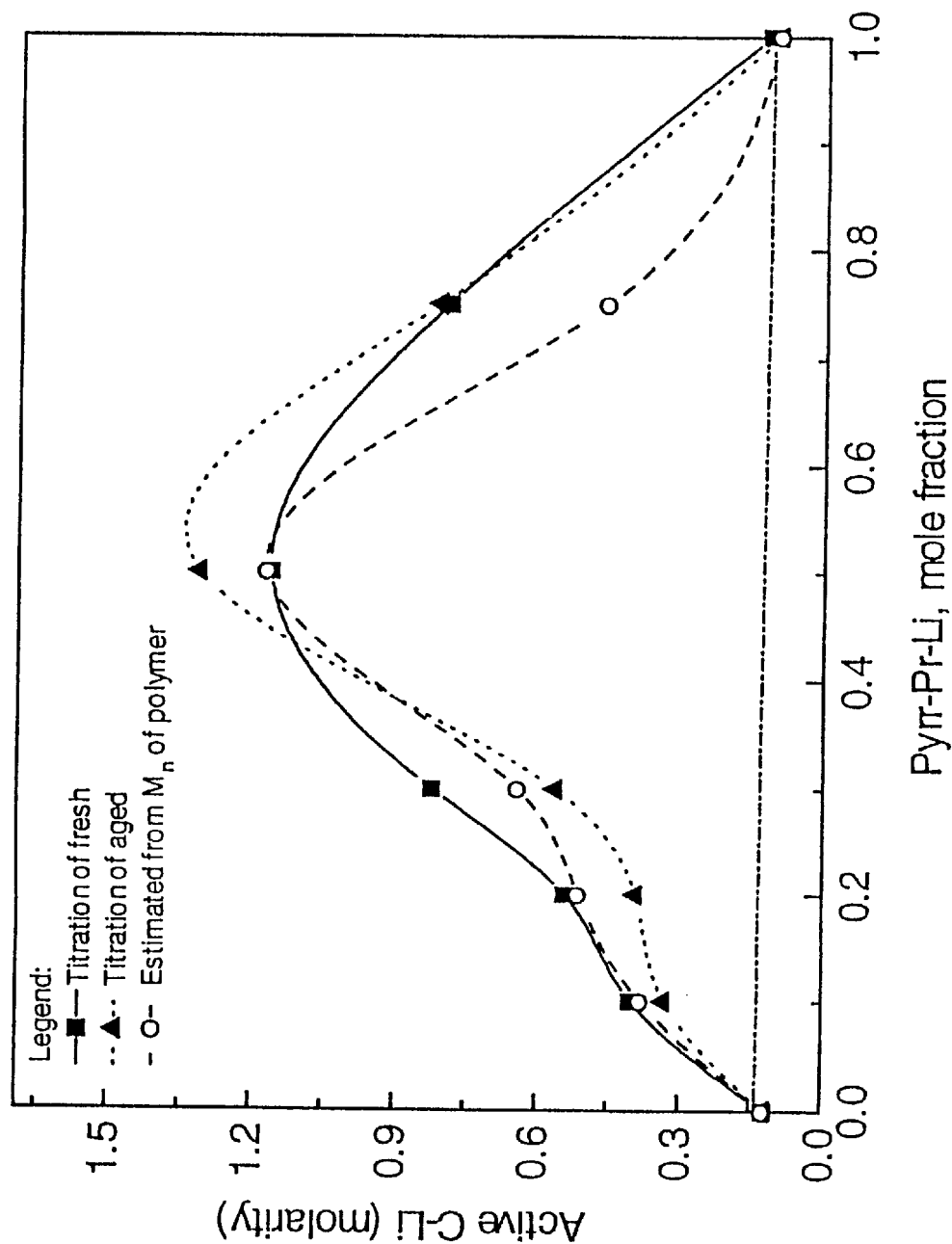

METHOD OF PREPARING A POLYMER USING ALIPHATIC SOLUTIONS OF AMINOALKYLLITHIUM COMPOUNDS

This application is a continuation of application Ser. No. 08/904,497, filed Aug. 1, 1997, now U.S. Pat. No. 5,935,893.

TECHNICAL FIELD

This invention relates to aliphatic solutions containing cyclic amine alkyllithium compounds that are useful for anionic polymerization. Specifically, the solutions of the present invention contain at least two different initiator compounds, one of which is a cyclic amine alkyllithium compound. The aliphatic solutions of the present invention are improved over known solutions because they can be stored, transported and reacted at highly concentrated levels.

BACKGROUND OF THE INVENTION

It is well known in the art that polymers can be prepared by anionic polymerization employing organolithium compounds such as butyllithium. It is also known in the art that such polymers can be prepared and functionalized using particular initiators that impart a functional group on the polymer.

For example, it is desirable to produce elastomeric compounds exhibiting reduced hysteresis characteristics. Such elastomers, when used to form articles such as tires, power belts and the like, will show an increase in rebound, a decrease in rolling resistance, and will have less heat build-up when mechanical stresses are applied.

It is believed that hysteretic power loss results from that section of the polymer chain from the last cross-link of the vulcanizate to the end of the polymer chain. This free end cannot be involved in an efficient, elastically recoverable process, and as a result, any energy transmitted to this section of the vulcanizate is lost as heat.

One method of reducing such hysteretic power loss is to provide the polymer chain with a functional group that will interact with other substances compounded with the vulcanizate, e.g., carbon black, and thereby serve to stabilize that section of the vulcanizate between the end of the polymer chain and the last cross-link. This functional group can, for example, be achieved by anionically polymerizing the polymer with a cyclic lithioamine initiator, which technique is generally described in U.S. Pat. No. 5,329,005.

In the art of manufacturing rubber, temperatures during polymerization and processing can reach 50–120° C. At these temperatures, some cyclic lithioamine functional groups can undergo elimination of the amine, resulting in a disruption of the polymerization process and/or loss of the polymer-bound amino content.

Although many functional groups have been contemplated that would impart hysteretic loss reducing properties to vulcanizates, the initiators from which the functional groups ultimately derive must be soluble in solvents conducive to anionic polymerization. To address this issue, U.S. Pat. No. 5,332,810 teaches an anionic polymerization initiator that is soluble in acyclic alkane solvents. This particular initiator is the reaction product of an amine, an organolithium and a solubilizing component. The solubilizing component may be a hydrocarbon, an ether, an amine, or a mixture thereof.

Likewise, U.S. Pat. No. 5,578,542 teaches a mixed amine system, where otherwise non-soluble metal amides are rendered soluble when mixed with other metal amides. It has been found that such mixed amine systems increase solubility by about two-fold, thereby delaying the onset of visible precipitation for a period of days, and even weeks, at room temperature in hexanes.

U.S. Pat. No. 5,550,203 teaches an anionic polymerization initiator that is chain extended. The chain extension results in improved solubility of the initiator in hydrocarbon solvents and an increased rate of polymerization when Such initiators are employed. It has been found, however, that refrigeration of these initiators within a hydrocarbon solvent is required for storage because decomposition of the initiator can occur.

SUMMARY OF INVENTION

It is therefore, an object of the present invention to provide a solution containing cyclic aminoalkyllithium compounds.

It is another object of the present invention to provide an aliphatic solution of cyclic aminoalkyllithium compounds having improved solubility over solutions known heretofore in the art.

It is yet another object of the present invention to provide an aliphatic solution of cyclic aminoalkyllithium compounds that exhibit improved solubility at 0° C.

It is still another object to provide an aliphatic solution of cyclic aminoalkyllithium compounds that exhibit improved solubility at 0° C. for periods greater than one week.

It is yet another object to provide an aliphatic solution of cyclic aminoalkyllithium compounds that can be stored at temperatures up to about 40° C. for periods of more than a week without significant decomposition or precipitation.

It is yet another object to provide a method for preparing a highly concentrated aliphatic solution of cyclic aminoalkyllithium compounds.

It is still yet another object to provide a method for preparing cyclic aminoalkyllithium compounds and thereby achieve a highly concentrated aliphatic solution thereof without further processing.

At least one or more of the foregoing objects, together with the advantages thereof over the known art relating to aminoalkyllithium compounds and solutions thereof, which shall become apparent from the specification which follows, are accomplished by the invention as hereinafter described and claimed.

In general the present invention provides a method for reducing the amount of aliphatic solvent needed for maintaining aminoalkyllithium initiators in solution comprising the step of combining at least one aminoalkyllithium compound with a second, dissimilar lithioamine, wherein the aminoalkyllithium compound is defined by a formula selected from the group consisting of formulas I and II

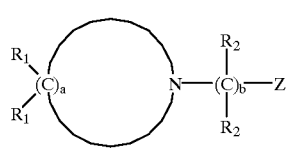

(I)

-continued

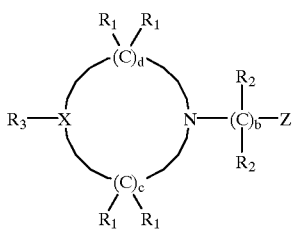
(II)

where Z is a lithium atom (Li); where X is an heteroatom selected from the group consisting of sulfur, oxygen and nitrogen; each $R_1$ is independently selected from the group consisting of hydrogen, and organic groups containing from 1 to about 12 carbon atoms; each $R_2$ is independently selected from the group consisting of hydrogen and organic groups containing from about 1 to about 4 carbon atoms; $R_3$ is independently selected from the group consisting of hydrogen and organic groups containing from 1 to about 6 carbon atoms and is only present where X is nitrogen; a is an integer from 5 to about 20; b is an integer from 1 to about 20; and c and d are integers from 1 to about 20, where the sum of c and d is from about 3 to about 20.

The present invention also includes a mixed lithioamine system comprising a first component, which is an aminoalkyllithium compound, and defined by a formula selected from the group consisting of formulas I and II

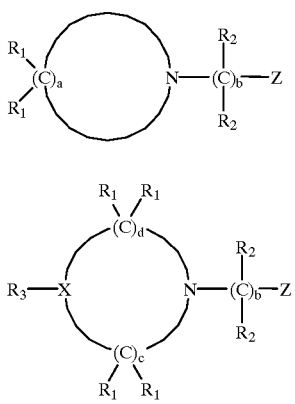
(I)

(II)

where Z is a lithium atom (Li); where X is an heteroatom selected from the group consisting of sulfur, oxygen and nitrogen; each $R_1$ is independently selected from the group consisting of hydrogen, and organic groups containing from 1 to about 12 carbon atoms; each $R_2$ is independently selected from the group consisting of hydrogen and organic groups containing from about 1 to about 4 carbon atoms; $R_3$ is independently selected from the group consisting of hydrogen and organic groups containing from 1 to about 6 carbon atoms and is only present where X is nitrogen; a is an integer from 5 to about 20; b is an integer from 1 to about 20; and c and d are integers from 1 to about 20, where the sum of c and d is from about 3 to about 20; a second component selected form the group consisting of cyclic lithioamines, dialkyl lithioamines, cyclic aminoalkyllithium compounds, dialkylaminoalkyllithium compounds, cyclic amino side-chain lithium compounds and cyclic amino side-chain alkyllithium compounds; and an aliphatic solvent.

The present invention further provides a method of preparing a mixed lithioamine system comprising the steps of combining at least two halogenated amines, within a solvent, wherein a first halogenated amine is defined by a formula selected from the groups consisting of formulas I and II

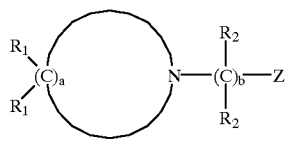
(I)

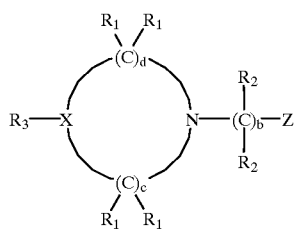
(II)

where z is a halide; where X is an heteroatom selected from the group consisting of sulfur, oxygen and nitrogen; each $R_1$ is independently selected from the group consisting of hydrogen, and organic groups containing from 1 to about 12 carbon atoms; each $R_2$ is independently selected from the group consisting of hydrogen and organic groups containing from about 1 to about 4 carbon atoms; $R_3$ is independently selected from the group consisting of hydrogen and organic groups containing from 1 to about 6 carbon atoms and is only present where X is nitrogen; a is an integer from 5 to about 20; b is an integer from 1 to about 20; and c and d are integers from 1 to about 20, where the sum of c and d is from about 3 to about 20, and wherein a second halogenated amine is different from the first halogenated amine and is selected from the group consisting of cyclic lithioamines, dialkyl lithioamines, cyclic aminoalkyllithium compounds, dialkylaminoalkyllithium compounds, cyclic amino side-chain lithium compounds and cyclic amino side-chain alkyllithium compounds; and reacting the halogenated amines with a lithio reactant.

BRIEF DESCRIPTION OF THE DRAWINGS

FIG. 1 is a graphical representation of the solubility of mixtures of hexamethyleneiminopropyllithium and pyrrolidinopropyllithium.

PREFERRED EMBODIMENT FOR CARRYING OUT THE INVENTION

It has now been found that the solubility of aminoalkyllithium compounds, or tertiary cyclic aminoalkyllithium compounds, in alkane solvents, particularly cycloalkane solvents, can be increased by preparing a system containing at least one aminoalkyllithium compound and at least one other amine containing compound that is different from the first aminoalkyllithium compound. This increase in solubility is particularly advantageous in the art inasmuch as the amount of solvent employed to synthesize, transport, and utilize such compounds is greatly reduced, and/or the need for refrigeration to stabilize such compounds in solution is obviated.

Aliphatic solvent solutions containing aminoalkyllithium compounds, to which the present invention is directed, will be referred to as mixed lithioamine systems because the solutions contain at least two different lithioamine compounds, one of which is an aminoalkyllithium compound. Specifically, the mixed lithioamine systems contain at least one alkyllithium compound that is a cyclic aminoalkyllithium compound. The cyclic aminoalkyllithium compounds, discussed hereinbelow, will simply be referred to as the first component of the mixed lithioamine system.

In one embodiment, which is especially preferred, the first component can generally be defined by the formula I

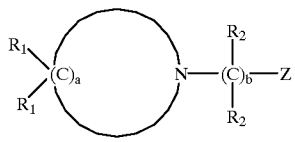
(I)

where Z is a lithium atom (Li); each $R_1$ is independently selected from the group consisting of hydrogen, and organic groups containing from 1 to about 12 carbon atoms; each $R_2$ is independently selected from the group consisting of hydrogen and organic groups containing from about 1 to about 12 carbon atoms; a is an integer from about 5 to about 20; and b is an integer from 1 to about 20. It should be appreciated that each $R_1$ and $R_2$ are of the same scope with the exception that $R_1$ can provide a bridging bond, however, $R_2$ is preferably hydrogen or a short organic group containing from 1 to about 4 carbon atoms. Preferably a is an integer from about 6 to about 16, and b is an integer from about 3 to about 12, and even more preferably a is an integer from about 6 to about 12.

With reference to those substituents that are independently selected, it should be understood that each substituent is separately selected without reference to any other substituent. For example, where a is five, nine of the $R_1$s can be hydrogen atoms while the tenth can be an ethyl or other alkyl group. Likewise, where b is three, five of the $R_2$s can be hydrogen atoms while the sixth can be an alkyl group such as methyl.

The organic groups defined herein can contain unsaturation, but are preferably branched, straight chain, or cyclic alkyl groups. It should be further understood that the organic groups can contain heteroatoms including oxygen, sulfur and nitrogen. For example, the organic groups of the present invention can include tertiary amines, simple alkyl or alkenyl, cycloalkyl or cycloalkenyl, bicycloalkyl or bicycloalkenyl or aralkyl groups, and other non-interfering oxygen, nitrogen, and sulfur containing analogs. Examples of such groups include hexyl moieties, propyl moieties, and isobutyl moieties. Although the preceding examples of possible organic radical groups have been recited, the scope of the invention should not be limited thereto.

Accordingly, the aminoalkyllithium compounds that are especially preferred include hexamethyleneiminopropyllitliium,

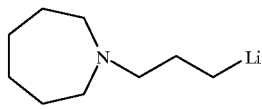

hexamethyleneiminohexyllithium,

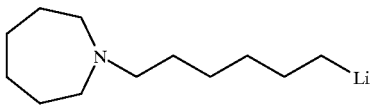

dodecamethyleneiminopropyllithium,

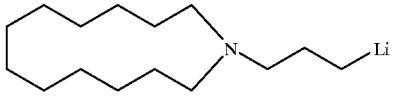

(3,3,5-trimethyl-hexamethylene-imino)propyl lithium,

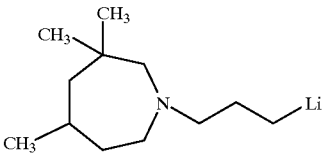

piperidinopropyllithium,

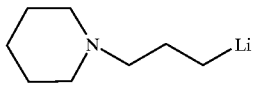

and 3 methyl-piperidinopropyllithium

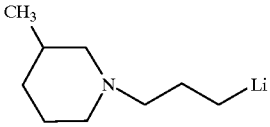

In another embodiment, the first component includes those compounds generally defined by the formula II

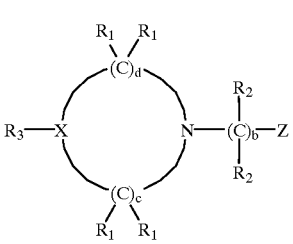
(II)

where Z is a lithium atom (Li); where X is an heteroatom selected from the group consisting of sulfur, oxygen and nitrogen; each $R_1$ is independently selected from the group consisting of hydrogen, and organic groups containing from 1 to about 12 carbon atoms; each $R_2$ is independently selected from the group consisting of hydrogen and organic groups containing from about 1 to about 4 carbon atoms; $R_3$ is independently selected from the group consisting of hydrogen and organic groups containing from 1 to about 6 carbon atoms and is only present where X is nitrogen; b is an integer from 1 to about 20; c is an integer from 1 to about 20, and d is an integer from 1 to about 20, where the sum of c and d is from about 3 to about 20. Preferably, b is an integer from about 2 to about 6, and c and d are integers from about 2 to about 6, where the sum of c and d is from about 4 to about 12. It should be appreciated that each $R_1$ and $R_2$ are of the same scope with the exception that $R_2$ is preferably hydrogen or a short organic group containing from 1 to about 4 carbon atoms.

Examples of compounds that are generally represented by the formula II include, but are not limited to, various mono N-alkyl derivatives of homopiperazine (1,4-diazacycloheptane), and ring C-substituted N-alkylhomopiperazines (1,4-diazacycloheptanes). Still other examples include various mono N-alkyl derivatives of 1,4-, or 1,5-diazacyclooctanes, and ring C-substituted 1,4-, or 1,5-diazacyclooctanes. Other examples still include various mono N-alkyl derivatives of piperazine, especially with N-alkyl groups of propyl or larger, and ring C-substituted N-alkylpiperazines.

It should be understood that the cyclic compounds discussed herein, such as formula I, can also include multicyclic compounds such as bi-cyclic and tri-cyclic compounds. Accordingly, it should be understood that formula I, for example, can be defined where Z is a lithium atom (Li); each $R_1$ is independently selected from the group consisting of hydrogen, organic groups containing from 1 to about 4 carbon atoms, and a bridging bond; each $R_2$ is independently selected from the group consisting of hydrogen and organic groups containing from about 1 to about 4 carbon atoms; a is an integer from 1 to about 20; and b is an integer from 2 to about 20; and optionally including a bridge, formed by the selection of two of said bridging bonds; the bridge having 0 to about 6 carbon atoms between the bridging ring members. It should be appreciated that each $R_1$ and $R_2$ are of the same scope with the exception that $R_1$ can provide a bridging bond, however, $R_2$ is preferably hydrogen or a short organic group containing from 1 to about 4 carbon atoms. It should be understood that the amino ring can contain up to 20 ring carbon atoms in addition to the ring nitrogen, thereby forming a 21 member ring.

Regarding the use of the bridging bond, it should be appreciated that compounds represented by formula I can include multi-cyclo compounds such as bicyclo and tricyclo compounds. It should be understood that two connected $R_1$ groups will represent a bridge between two ring members. In a case where there is a direct bond between two ring members, without wishing to be bound by any particular theory, the $R_1$ variables simply represent an electron contributed to the bridge, which is a direct bond between ring members. Where the bridge formed between ring members includes an organic group, it should be understood that $R_1$ and $R_2$ provide a bonding site where the bridge is joined to the ring; again via the contribution of an electron. In view of this teaching, the use of the term substituent, as it relates to $R_1$ should be interpreted so as to include atoms, organic moieties and bonding sites or electrons. As an example, two $R_2$ bridging bonds can form a bridge across the cyclic amino ring, thereby creating a bicyclo compound. This bridge between ring carbons can include zero carbon atoms, in which case there is a direct bond between ring carbons. The bridge can also include up to about 4 carbon atoms, in which case the bridge comprises an organic group. Those of ordinary skill in the art will understand that inasmuch as a $R_1$ substituent contributes to a bridge, it will no longer be available as a hydrogen or organic group extending from the ring.

As discussed above, the mixed lithio amine system contains at least two different aminoalkyllithium compounds, one of which has been referred to as the first component. The mixed lithio amine system of the present invention also includes a second component. The second component, or other lithioamine compound, can include any other lilhioamine compound that is useful for initiating an anionic polymerization and increases the overall solubility of the mixture when mixed with the first component.

Specifically, the second component of the lithioamine system can include compounds such as cyclic lithioamines, dialkyl lithioamines, cyclic aminoalkyllithium compounds, dialkylaminoalkyllithium compounds, and cyclic amino side-chain lithium compounds and cyclic amino side-chain alkyllithium compounds. Where the cyclic aminoalkyllithium compounds are employed as the second component, the cyclic aminoalkyllithium compound must be different than the cyclic aminoalkyllithium compound of the first component. Other compounds include aryllithiums and alkyllithiums and alkenyl lithiums.

Cyclic lithioamines and dialkyl lithioamines that can be employed as the second component include those described in U.S. Pat. Nos. 5,332,810, 5,329,005, and 5,578,542, which are incorporated herein by reference. Cyclic aminoalkyllithium compounds and dialkyl aminoalkyllithium compounds include those described in U.S. Pat. No. 5,496,940, which is incorporated herein by reference. The cyclic amino side-chain lithium compounds and alkyllithium compounds include those described in copending U.S. Ser. No. 08/777,656, U.S. Pat. No. 5,786,441 which is likewise incorporated herein by reference.

In a preferred embodiment, the second component of the mixed lithioamine system of the present invention is an aminoalkyllithium compound generally described by the formulas I and II, hereinabove, with the exception that a is an integer from about 2 to about 20; and b is an integer from 1 to about 20. Preferably, a is an integer from about 4 to about 12, and b is an integer from about 3 to about 12.

It should be understood, however, that when the second component includes a compound generally described by the formulas I or II, hereinabove, at least one of the variables $R_1$, $R_2$, b, c, or d must be different than that of the first component. In other words, the molecule of the first component must be different than the molecule of the second component. It is most preferred that the variable (a) differ, it is less preferred that the variable $R_1$ differ, it is even less preferred that the variable (b) differ, and it is least preferred that the variable $R_2$ differ, although a change in any of the variables will satisfy the requirements of this invention.

Inasmuch as the mixed lithio amine system of the present invention contains at least two different lithioamine compounds, it should be understood that the system can include more than two lithioamine compounds, with the proviso that at least one of the compounds include those defined as the first component and the other compounds differ from the first component.

With respect to the relative amounts of the first and second components within the mixed lithioamine system of the present invention, the molar ratio of the first component to the second component can be in the range from about 95:5 to about 5:95. It is preferred, however, that the first component be the major component of the system. Accordingly, it is preferred that the molar ratio of the first component to the second component be in the range from about 95:5 to about 50:50. Even more preferably, the molar ratio of the first component to the second component is in the range from about 90:10 to about 50:50, still more preferably in the range from about 80:20 to about 50:50, and even more preferably from about 70:30 to about 50:50.

An unexpected discovery associated with the mixed amine system of the present invention is that in the preferred range the solubility of the amine compounds within aliphatic solvents increases by a factor of greater than about two (2) over the solubility of the compounds individually within such solvents. Preferably, the solubility increases by a factor of greater than about two and a half (2.5), more preferably the solubility increases by a factor of greater than about three (3), and even more preferably the solubility increases by a factor of greater than about three and a half (3.5). It should be understood that a corresponding decrease in required solvent will be observed with increased solubility of the mixed lithioamine system of the present invention. In other words, there is an inverse relationship between increasing solubility and the amount of solvent necessary to maintain the lithioamines in solution. As those skilled in the art will appreciate, substantial efficiency and cost savings are expected as a result of the reduced amount of solvent needed to prepare, store, transport, and use lithioamines when practicing the present invention.

For purposes of this specification, the term solubility refers to the maximum concentration of the mixed lithioamine system (moles/liter) that can be sustained in aliphatic or cycloaliphatic solvents over a range of temperatures and for an extended period of time. For purposes of this definition, the time period contemplated is from about 2 to about 21 days and the temperature range contemplated is from about 0° C. to about 45° C. One significant advantage of the present invention is that increased insolubility is observed, without decomposition or instability of the lithioamines, without the need for refrigeration. In other words, storage and transportation of the mixed lithioamine system can occur at temperatures up to about 30° C., and even up to about 40° C.

It should be understood that the increase in solubility observed with respect to the mixed lithioamine systems of the present invention is an increase with respect to the solubility of the compounds individually within such solvents. Inasmuch as there are at least two compounds within this system, the increase at any given ratio of components is compared to the hypothetical curve derived by drawing a straight line between the separate solubility measurement of the individual components. For example, with reference to the Figure, the separate solubility of hexamethyleneiminopropyllithium is indicated at that location on the graph where the concentration of pyrrolidinopropyllithium is zero. Likewise, the Figure indicates the separate solubility of pyrrolidinopropyllithium where the concentration of pyrrolidinopropyllithium is 100 percent of the system. The straight dashed line connecting these two points is the hypothetical curve derived by drawing a straight line between the separate solubilities of the individual components of that system.

As used herein, the term aliphatic solvent includes straight chain and branched chain organic solvents that are conducive for anionic polymerization. Other solvents that are useful for practicing the present invention include cycloaliphatic solvents, such as cyclohexane, which is preferred. More broadly, the solvents that are useful for preparing the initiator solutions of the present invention include all non-polar organic solvents.

Typically, aminoalkyllithium compounds are employed as initiators for anionic polymerization of diene and vinylaromatic polymers. Accordingly, it is preferred to use the mixed amine system of the present invention as an initiator system to initiate the anionic polymerization of dienes and/or vinylaromatic compounds, such as isoprene, 1,3-butadiene, styrene, etc. The living polymers that result from such polymerization may be further functionalized by treatment with suitable reagents known in the art. The products, when compounded, will give vulcanizates or elastomeric compositions with reduced hysteresis.

The lithioamine compounds employed in the present invention can be formed by any number of techniques as described in those references incorporated herein. With specific regard to the cyclic aminoalkyllithium compounds, such as those employed in the first components of the mixed lithioamine system of the present invention, the preferred method of preparing these compounds includes reacting a cyclic aminoalkylhalide with a lithio reactant selected from elemental lithium metal, an organo-lithium compound, and mixtures thereof. The cyclic aminoalkylhalide or amino reagent can generally be represented by the formula I, hereinabove, where Z is a halide selected from bromine, chlorine, iodine, or the like, preferably bromine or chlorine.

When reacted with elemental lithium metal in a suitable solvent such as hexane, cyclohexane, ethers or the like, the resulting reduction reaction produces a lithiated cyclic amine compound as generally represented by the formulas I and II, above, where Z is lithium.

In the alternative, the amino reagent can also be reacted with an organolithium reactant having the general formula RLi, again in a suitable solvent such as those described hereinabove. RLi can be, for example, selected from the group consisting of alkyls, cycloalkyls, alkenyls, aryls and aralkyls having from 1 to about 20 carbons atoms in short chain length low molecular weight polymers from diolefin and vinyl aryl monomers having up to about 25 units. Typical alkyls include n-butyl, s-butyl, t-butyl, methyl, ethyl, isopropyl and the like. The cycloalkyls include cyclohexyl, menthyl and the like. The alkenyls include allyl, vinyl and the like. The aryl and aralkyl groups include phenol, benzyl, oligo(styryl) and the like. Exemplary short chain length polymers include the oligo(butadienyls), oligo(isoprenyls), oligo(slyryls) and the like. Alkyllithium reactants such as t-butyllithium are preferred.

Typically, the two components are allowed to react for up to about 24 hours at low to ambient temperatures (−7° C.–30° C.), or elevated temperatures up to about 100° C., preferably less than 50° C., and more preferably less than about 38° C.

If one atom equivalent of lithium in the organolithium reactant is used per atom equivalent of aminoalkylhalide, a product of the reaction will be an organohalide, that may be undesirable for the intended use of the inventive compound. It may therefore, be preferable to employ two or more atom equivalents of lithium from the organolithium reactant per atom equivalent of aminoalkylhalide. It is believed that a reaction with an excess of lithium will result in a lithium halide and other low molecular weight hydrocarbon byproducts, which may be more acceptable for the intended use of the inventive compounds.

Such cyclic alkylamino compounds are either prepared in combination, or once they are prepared they are combined to form the mixed amine system of the present invention. Inasmuch as the solubility of the compounds is increased upon mixing, the solutions may have to be heated to supersaturation before they are combined. In the alternative, solvents can be removed from the combined solutions using vacuum distillation.

Rather than combine the lithiated cyclic alkylamine compounds after individual preparation thereof, it is most preferred to combine the reactants, i.e., the halogenated reactants, in solution prior to lithiation. Once this mixed reagent system is prepared, the same can be reacted with about two atom equivalents of lithium metal or with two equivalents of an alkyllithium such as t-butyllithium. As a result of the increased solubility of the mixed halide system, the need to remove solvent once the lithioamines are prepared is obviated.

Additionally, the aminoalkyllithium compounds employed in the present invention can be prepared according to the procedure described in patent application Ser. No. 08/777,646, now U.S. Pat. No. 5,852,189, which is incorporated herein by reference. There, dimethyl ether is used as a solvent for the lithiation of tertiaryaminoalkylclhlorides at temperatures between about −78° C. and about −24° C. This synthetic preparation is particularly advantageous due to the volatility of ether, which facilitates removal of the solvent by evaporation. Once the ether is evaporated, the lithiated product is then dissolved in aliphatic hydrocarbon solvents.

As stated above, the mixed amine system of the present invention may be used as an initiator system to prepare any anionically-polymerizable polymer, e.g., homopolymers of polybutadiene, polyisoprene and the like, and copolymers thereof with monovinyl aromatics such as styrene, alpha methyl styrene and the like, or trienes such as myrcene, and mixtures of the foregoing. Suitable monomers include conjugated dienes having from about 4 to about 12 carbon atoms, monovinyl aromatic monomers having 8 to 18 carbon atoms and trienes. Examples of conjugated diene monomers and the like useful in the present invention include 1,3-butadiene, isoprene, 1,3-pentadiene, 2,3-dimethyl-1,3-butadiene and 1,3-hexadiene, and aromatic vinyl monomers include styrene, alpha-methylstyrene, p-methylstyrene, vinyltoluene, and vinylnaphthalene. The conjugated diene monomer and aromatic vinyl monomer are normally used at the weight ratios of 95–50:5–50, preferably 95–65:5–35, respectively. Adducts of the initiator with monomers that do not homopolymerize, e.g. 1,1-diphenylethylene and substituted 1,1-diphenylethylenes, are also considered to be initiators of this invention.

Polymerization is conducted in polar or non-polar solvent, such as tetrahydrofuran (THF), a hydrocarbon solvent, such as the various cyclic and acyclic hexanes, heptanes, octanes, pentanes, their alkylated derivatives, and mixtures thereof. In order to promote randomization in copolymerization and to control vinyl content, a polar coordinator may be added to the polymerization ingredients. Amounts range between 0 and 90 or more equivalents per equivalent of lithium. The amount depends on the amount of vinyl desired, the level of styrene employed and the temperature of the polymerization, as well as the nature of the specific polar coordinator (modifier) employed. Suitable polymerization modifiers include, for example, ethers or amines to provide the desired microstructure and randomization of the comonomer units. The molecular weight of the polymer ("base polymer") that is produced in this invention is optimally such that a proton-quenched sample will exhibit a gum Mooney (ML/4/100) of from about 1 to about 150. However, useful lower molecular weight compounds can also be made using these initiators. These might typically be considered fluids, having molecular weights ranging from several hundreds to tens of thousands of mass units. They can be used as viscosity modifiers and as dispersants for particulates, such as carbon black in oil.

Polymers of the present invention can be of any molecular weight, depending on the intended application. Generally, for purposes of making tire products, the molecular weight of the polymer should fall within the range from about 50,000 to about 1,000,000 preferably from 80,000 to about 500,000 and most preferably from about 100,000 to about 250,000. When used as a viscosity modifier, the molecular weight of the polymer should generally fall within the range from about 500 to about 50,000, preferably from about 1,500 to about 30,000 and most preferably from about 2,000 to about 15,000.

Other compounds useful as polar coordinators are organic and include tetrahydrofuran (THF), linear and cyclic oligomeric oxolanyl alkanes such as 2,2-bis(2'-tetrahydrofuryl) propane, dipiperidyl ethane, dipiperidyl methane, hexamethylphosphoramide, N-N'-dimethylpiperazine, diazabicyclooctane, dimethyl ether, diethyl ether, tributylamine and the like. The linear and cyclic oligomeric oxolanyl alkane modifiers are described in U.S. Pat. No. 4,429,091, owned by the Assignee of record, the subject matter of which relating to such modifiers is incorporated herein by reference. Compounds useful as polar coordinators include those having an oxygen or nitrogen hetero-atom and a non-bonded pair of electrons. Other examples include dialkyl ethers of mono and oligo alkylene glycols; "crown" ethers; tertiary amines such as tetramethylethylene diamine (TMEDA); linear THF oligomers; and the like.

A batch polymerization is begun by charging a blend of monomer(s) and normal alkane solvent to a suitable reaction vessel, followed by the addition of the polar coordinator (if employed) and the initiator compound previously described. The reactants are heated to a temperature of from about 20 to about 200° C., and the polymerization is allowed to proceed for from about 0.1 to about 24 hours. This reaction produces a reactive polymer having a lithium atom at the reactive or living end thereof.

At the non-living end, the polymer will include a functional group derived from the initiator. Thus, for example, a resulting polymer molecule of the present invention can be represented by formula I, hereinabove, where Z is a living polymer chain having a lithium atom (Li) at its growing end; and the other substituents are as defined above. The polymer is any anionically-polymerized polymer including, for example, those derived from diene homopolymers, monovinyl aromatic polymers, diene/monovinyl aromatic random copolymers and block copolymers.

Further monomer addition at the living lithium end causes the molecular weight of the polymer to increase as the polymerization continues. To terminate the polymerization, and thus further control polymer molecular weight, a terminating agent, coupling agent or linking agent may be employed, all of these agents being collectively referred to herein as "terminating reagents". Termination of anionically polymerized living polymers having a lithium atom at a living end is well known in the art.

For example, polymers according to the present invention can be defined by formula I, hereinabove, where Z is a terminated polymer; and the other substituents are as defined above.

Certain terminating reagents may provide the resulting polymer with a multifunctionality. That is, the polymers initiated according to the present invention may carry at least one amine functional group, that is, the polymers initiated according to the present invention may carry at least one amine functional group derived from an initiator, and may also carry a second functional group selected and derived from the group consisting of terminating reagents, coupling agents and linking agents. In addition to the terminating agents described hereinbelow, terminating agents including cyclic amines may also be employed.

Useful terminating reagents include active hydrogen compounds such as water or alcohol; carbon dioxide; toluene diisocyanate (TDI); N,N,N',N'-tetra-alkyldiamino-benzophenone, such as tetramethyldiamino-benzophenone or the like; N,N-dialkylamino-benzaldehyde, such as dimethylamino-benzaldehyde or the like; 1,3-dialkyl-2-imidazolidinones, such as 1,3-dimethyl-2-imidazolidinone (DMI) or the like; 1-alkyl substituted pyrrolidinones, such as N-methyl pyrrolidinone (NMP); 1-aryl substituted pyrrolidinones; dialkyl- and dicycloalkyl-carbodiimides having from about 5 to about 20 carbon atoms, such as 1,3-dicyclohexyl carbodiimide (DCCD); as well as the following:

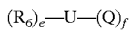

where U is tin or silicon. It is preferred that U is tin. $R_6$ is an alkyl having from about 1 to about 20 carbon atoms; a cycloalkyl having from about 3 to about 20 carbon atoms; an aryl having from about 6 to about 20 carbon atoms; or, an aralkyl having from about 7 to about 20 carbon atoms. For example, $R_6$ may include methyl, ethyl, n-butyl, neophyl, phenyl, cyclohexyl or the like. Q is chlorine or bromine, "e" is from 0 to 3, and "f" is from about 1 to 4; where e+f=4.

Further, additional terminators include compounds expressed by the formulae

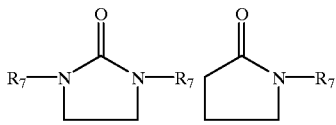

where each $R_7$ is the same or different and is an alkyl, cycloalkyl or aryl, having from about 1 to about 12 carbon atoms. For example, $R_7$ may include methyl, ethyl, nonyl, t-butyl, phenyl or the like. It should be appreciated that when $R_7$ is methyl, the above molecules are 1,3-dimethyl imidazolidinone (DMI) and N-methylpyrrolidine (NMP), respectively.

Additional terminators also include

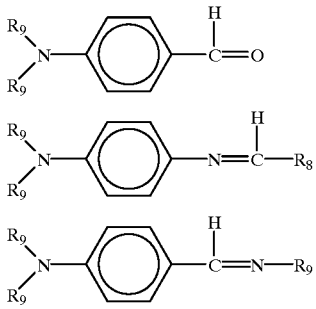

where $R_8$ is an alkyl, phenyl, alkylphenyl or dialkylaminophenyl, having from about 1 to about 20 carbon atoms. For example, $R_8$ may include t-butyl, 2-methyl-4-pentene-2-yl, phenyl, p-tolyl, p-butylphenyl, p-dodecylphenyl, p-diethylaminophenyl, p-(pyrrolidino) phenyl, and the like. Each $R_9$ is the same or different, and is an alkyl or cycloalkyl having from about 1 to about 12 carbon atoms. Two of the $R_9$ groups may together form a cyclic group. For example, $R_9$ may include methyl, ethyl, octyl, tetramethylene, pentamethylene, cyclohexyl or the like. When the $R_9$ groups are linked together as tetramethylene, it should be appreciated that the amino substituent is pyrrolidino.

Other examples of useful terminating reagents include tin tetrachloride, $(R_{10})_3SnCl$, $(R_{10})_2SnCl_2$, $R_{10}SnCl_3$, carbodiimides, cyclic amides, cyclic ureas, isocyanates, Schiff bases, 4,4'-bis(diethylamino) benzophenone, and the like, where $R_{10}$ is an alkyl, cycloalkyl or aralkyl having from 1 to about 12 carbon atoms, and other reactive hysteresis-reducing terminating compounds which may contain other heteroatoms such as oxygen, nitrogen, sulfur, phosphorus, tin, non-interfering halogen, etc. Suitable terminating reagents also include the isomeric vinylpyridines, other (bis)dialkylamino-benzophenones (e.g., Michler's ketone), etc. Exemplary amino groups formed by reaction with a terminating group that forms an amine includes any of the foregoing amine containing compounds, such as TDI, NMP, DMI, DCCD and the like When the living polymer is coupled with or end-linked with any of the various known coupling reagents, such as silicon tetrachloride, tin tetrachloride, etc., symmetrically "dicapped" polymers are prepared. When end-linking polymers through reaction with for example, $(R_5)_e SnQ_f$, $SnCl_4$, or $C_4H_9SnCl_3$ to obtain products with substantially greater than 10 percent/end-linking through tin, especially desirable elastomeric compositions with low hysteresis properties are prepared. $(R_5)_e SnQ_f$ is defined, where $R_5$ is selected from the group consisting of alkyls, cycloalkyls, alkenyls, aryls and aralkyls having from 1 to about 20 carbon atoms and short chain length low molecular weight polymers from diolefin and vinyl aryl monomers having up to about 25 units, and Q, e and f are as described hereinabove.

The terminating reagent is added to the reaction vessel, and the vessel is agitated for about 1 to about 1000 minutes. As a result, an elastomer is produced having an even greater affinity for compounding materials such as carbon black, and hence, even further reduced hysteresis. Additional examples of terminating reagents include those found in U.S. Pat. No. 4,616,069 which is herein incorporated by reference for the disclosure of terminating agents.

The polymer may be separated from the solvent by conventional techniques. These include steam or alcohol coagulation, thermal desolventization, or any other suitable method. Additionally, solvent may be removed from the resulting polymer by drum drying, extruder drying, vacuum drying or the like.

The elastomers made from the anionic initiators of the present invention comprise a plurality of polymer molecules, having a functional group at the head, and preferably also, at the tail of the resulting polymer. Conventional compounding of such elastomers with fillers, and subsequent curings results in products exhibiting reduced hysteresis, which means a product having increased rebound, decreased rolling resistance and having less heat build-up when subjected to mechanical stress.

The polymers made from the anionic initiators of the present invention can be used alone or in combination with other elastomers to prepare a product such as a tire treadstock, sidewall stock or other tire component stock compound. Such stocks are useful for forming tire components such as treads, subtreads, black sidewalls, body ply skims, bead fillers and the like. At least one such component is produced from a vulcanizable elastomeric or rubber composition. For example, they can be blended with any conventionally employed treadstock rubber which includes natural rubber, synthetic rubber and blends thereof. Such rubbers are well known to those skilled in the art and include synthetic polyisoprene rubber, styrene/butadiene rubber (SBR), polybutadiene, butyl rubber, poly(chloroprene), ethylene/propylene rubber, ethylene/propylene/diene rubber (EPDM), acrylonitrile/butadiene rubber (NBR), silicone rubber, the fluoroelastomers, ethylene acrylic rubber, ethylene vinyl acetate copolymer (EVA), epichlorohydrin rubbers, chlorinated polyethylene rubbers, chlorosulfonated polyethylene rubbers, hydrogenated nitrile rubber, tetrafluoroethylene/propylene rubber and the like. When the polymers of the present invention are blended with conventional rubbers, the amounts can vary widely such as between 10 and 99 percent by weight of the former.

The polymers can be compounded with carbon black in amounts ranging from about 1 to about 100 parts by weight, per 100 parts of rubber (phr), with about 20 to about 80 phr being preferred and with about 40 to about 80 phr being most preferred. The carbon blacks may include any of the commonly available, commercially-produced carbon blacks but those having a surface area (EMSA) of at least 20 $m^2/g$ and more preferably at least 35 $m^2/g$ up to 200 $m^2/g$ or higher are preferred. Surface area values used in this application are those determined by ASTM test D-1765 using the cetyltrimethyl-ammonium bromide (CTAB) technique. Among the useful carbon blacks are furnace black, channel blacks and lamp blacks. More specifically, examples of the carbon blacks include super abrasion furnace (SAF) blacks, high abrasion furnace (HAF) blacks, fast extrusion furnace (FEF) blacks, fine furnace (FF) blacks, intermediate super abrasion furnace (ISAF) blacks, semi-reinforcing furnace (SRF) blacks, medium processing channel blacks, hard processing channel blacks and conducting channel blacks. Other carbon blacks which may be utilized include acetylene blacks. Mixtures of two or more of the above blacks can be used in preparing the carbon black products of the invention. Typical values for surface areas of usable carbon blacks are summarized in the following table.

| CARBON BLACKS | |
|---|---|
| ASTM Designation (D-1765-82a) | Surface Area ($m^2/g$) (D-3765) |
| N-110 | 126 |
| N-220 | 111 |
| N-339 | 95 |
| N-330 | 83 |
| N-550 | 42 |
| N-660 | 35 |

The carbon blacks utilized in the preparation of the rubber compounds used may be in pelletized form or an unpelletized flocculent mass. Preferably, for more uniform mixing, unpelletized carbon black is preferred. The reinforced rubber compounds can be cured in a conventional manner with known vulcanizing agents at about 0.5 to about 4 phr. For example, sulfur or peroxide-based curing systems may be employed. For a general disclosure of suitable vulcanizing agents one can refer to Kirk-Othmer, *Encyclopedia of Chemical Technology*, 3rd ed., Wiley Interscience, N.Y. 1982, Vol. 20, pp. 365–468, particularly "Vulcanization Agents and Auxiliary Materials" pp. 390–402. Vulcanizing agents may be used alone or in combination.

Vulcanizable elastomeric compositions made from the above elastomers can be prepared by compounding or mixing the polymers thereof with carbon black and other conventional rubber additives such as fillers such as silica, plasticizers, antioxidants, curing agents and the like, using standard rubber mixing equipment and procedures and conventional amounts of such additives.

The reinforced rubber compounds can be cured in a conventional manner with known vulcanizing agents at about 0.5 to about 4 phr. For example, sulfur or peroxide-based curing systems may be employed. For a general disclosure of suitable vulcanizing agents one can refer to Kirk-Othmer, *Encyclopedia of Chemical Technology*, 3rd ed., Wiley Interscience, N.Y. 1982, Vol. 20, pp. 365–468, particularly "Vulcanization Agents and Auxiliary Materials" pp. 390–402. Vulcanizing agents may be used alone or in combination. This invention does not affect cure times and thus the polymers can be cured for a conventional amount of time. Cured or crosslinked polymers will be referred to as vulcanizates for purposes of this disclosure.

In order to demonstrate the practice of the present invention, the following examples have been prepared and tested as described in the Experimental Section disclosed hereinbelow. The examples should not, however, be viewed as limiting the scope of the invention. The claims will serve to define the invention.

GENERAL EXPERIMENTATION

The preparation and increased solubility of the cyclic aminoalkyllithium compounds according to the present invention, as well as their use as initiators for anionic polymerization, was confirmed by preparing a number of cyclic alkylamino compounds. These compounds were then used as initiators to form a number of polymers.

EXAMPLE 1

A mixture of about 70:30 molar ratio of hexamethyleneiminopropylchloride and pyrrolidinopropylchloride, respectively, was lithiated using dimethyl ether as a solvent, at a temperature at about −25° C. Cyclohexane was added in an attempt to give a solution that approximated about 1 molar in concentration. Titration of the solution indicated that the solution was about 0.89 molar in active C—Li with 96 percent activity. GC and GC/MS analysis of the solution revealed that the solution was at least about 98 percent pure. The solution was then stored in a refrigerator at 0° C. for a period of about 3 weeks.

In order to determine the maximum solubility of the mixture at low temperature, the supernatant solution was re-titrated following the above-noted storage of three weeks. This titration occurred after the temperature of the solution was allowed to warm to near room temperature. The titration technique employed was a standard Gilman titration. The solution was found to be found to be 0.63 molar active in C—Li, with an activity of about 91 percent.

EXAMPLE 2

Polymerizations were run using the solubilized initiator solution generated in Example 1. Table I, hereinbelow, lists the ingredients and conditions used in the polymerizations, as well as the results observed using standardized testing. The 0.89 molar solution prepared in Example 1 was added to a dried, sealed, nitrogen-purged bottle, through a Viton rubber cap liner, to a 75:25 percent by weight blend of butadiene and styrene, respectively, in hexanes, at an estimated level of about 0.8 mequiv. Li/100 grams monomer. An additional amount of polar modifier was added.

The mixtures were agitated in the temperature range from about 50 to about 80° C. for about 2 to about 4 hours. This reaction resulted in at least about 90 percent conversion to polymer. As those skilled in the art will appreciate, there is considerable leeway in the reaction times and temperatures, much the same as there is leeway in the reaction vessels, type of agitation employed, etc. The cements were quenched by injection with 1.5 ml of isopropyl alcohol and treated with an antioxidant, which included 3 ml of a mixture containing about 1.6 weight percent DBPC in hexane. Some samples were also coagulated in isopropyl alcohol, air-dried at room temperature and then drum-dried.

TABLE I

| Example | Monomer (grams) | Target $M_n$, $10^3$ | Initiator, (ml) | $M_n$ obtained, $10^3$ | PDI | Calc. Initiator conc., (M) |
|---|---|---|---|---|---|---|
| 1-A | 69.5 | 120 | 0.67 | 155 | 1.19 | 0.67 |
| 1-B | 69.7 | 130 | 0.62 | 163 | 1.20 | 0.69 |
| 1-C | 71.5 | 130 | 0.64 | 155 | 1.23 | 0.72 |

Additional mixtures of hexamethyleneiminopropyllithium and pyrrolidinopropyllithium were prepared in exactly the same manner described in Example 1. These mixtures, identified as Examples 3–7, were prepared with the following respective molar ratios of hexamethyleneiminopropyllithium to pyrrolidinopropyllithium: 90:10, 80:20, 70:30, 50:50, and 25:75. The mixed aminoalkyllithium reagent solutions were titrated as prepared, i.e., "fresh," and the supernatant solutions after storage at 0° C. for two weeks, i.e., "aged," were also titrated. The same titration procedure described above was used.

The results of the titration of these mixtures, Examples 3–7 are summarized in Table II, hereinbelow. As discussed above, the ratio is that of hexamethyleneiminopropyllithium to pyrrolidinopropyllithium.

TABLE II

| Example | Ratio | Fresh: Active C—Li (M) | Aged: Active C—Li (M) |
|---|---|---|---|
| 3 | 90:10 | 0.4 | 0.33 |
| 4 | 80:20 | 0.54 | 0.39 |
| 5 | 70:30 | 0.76 | 0.56 |
| 6 | 50:50 | 1.16 | 1.31 |
| 7 | 25:75 | 0.79 | 0.81 |

As with Examples 1 and 2, the data of Table II shows that the solubilities of the mixtures are much greater than those of the individual components.

Table III, hereinbelow, summarizes the comparative results for hexamethyleneiminopropyllithium and pyrrolidinopropyllithium reagents prepared separately.

TABLE III

| Reagent | Ratio | Aged Active C—Li (M) |
|---|---|---|
| hexamethyleneiminopropyllithium | 100:0 | 0.12 |
| pyrrolidinopropyllithium | 0:100 | 0.10 |

EXAMPLES 8–12

The mixtures of Examples 3–7 were used to initiate the polymerizations of butadiene and styrene mixtures, in the same manner as in Example 2. From the molecular weights of the product of Examples 8–12, the active aminoalkyllithium concentrations were estimated. The results of such estimations, which are listed in Table IV, were generally similar to those of Table II that were found by titrations.

TABLE IV

| Example | Ratio | Pzn Results Estim. Calc. Initiator conc., (M) |
|---|---|---|
| 8 | 90:10 | 0.38 |
| 9 | 80:20 | 0.51 |
| 10 | 70:30 | 0.6 |
| 11 | 50:50 | 1.17 |
| 12 | 25:75 | 0.46 |

A marked increase in total solubility was obtained when the aminoalkyllithium initiator reagents were prepared as the mixture in accordance with the present invention as compared with the solubilities of the individual reagents.

EXAMPLES 13 AND 14

A hexamethyleneiminopropyllithium solution of increased solubility was also prepared by forming it in a mixture with 3,3,5-trimethylhexahydroazepinopropyllithium (THMI—Pr—Li). As indicated in Table V, hereinbelow, the ratio of hexamethyleneiminopropyllithium to THMI—Pr—Li was 75:25. As with the above Examples, Table V also summarizes the results of fresh and aged titrations.

TABLE V

| Example | A/B | Titration Results Fresh Active (M) | Titration Results Aged Active (M) |
|---|---|---|---|
| 13 | 75:25 | 0.60 | 0.63 |

In the same fashion as was performed in Example 2, a polymer was formed from the reagent of Example 13 and the initiator concentration was calculated based on the weight of the polymer. The result of this estimation is summarized in Table VI.

TABLE VI

| Example | A/B | Pzn Results Estim. (M) |
|---|---|---|
| 14 | 75:25 | 0.57 |

As with the above Examples, the mixture of hexamethyleneiminopropyllithium and THMI—Pr—Li shows an increase in solubility well above the individual solubilities of the reagents.

Thus, it should be evident that the mixed lithioamine system and related methods of the present invention are highly effective in reducing the amount of solvent necessary to maintain the mixed lithioamine system and solution. The invention is particularly suited for aliphatic solvents, but is not necessarily limited thereto.

Based upon the foregoing disclosure, it should now be apparent that the use of mixed lithioamine system described herein will carry out the objects set forth hereinabove. It is, therefore, to be understood that any variations evident fall within the scope of the claimed invention and thus, the selection of specific component elements can be determined without departing from the spirit of the invention herein disclosed and described. In particular, the second component of the present invention, which is a lithioamine, is not necessarily limited to those disclosed herein. Thus the scope of the invention shall include all modifications and variations that may fall within the scope of the attached claims.

What is claimed is:

1. A method of preparing a polymer comprising the steps of:

combining a mixed amine system with anionically-polymerizable monomers, said mixed amine system including a first and second component within a non-polar solvent, said first component is an aminoalkyllithium compound defined by a formula selected from the group consisting of formulas I and II

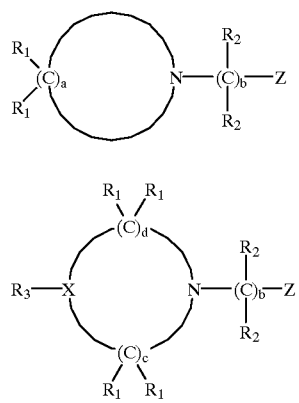

where Z is a lithium atom (Li); where X is an hetero atom selected from the group consisting of sulfur, oxygen and nitrogen; each $R_1$ is independently selected from the group consisting of hydrogen and organic groups containing from 1 to about 12 carbon atoms; each $R_2$ is independently selected from the group consisting of hydrogen and organic groups containing from 1 to about 4 carbon atoms; $R_3$ is independently selected from the group consisting of hydrogen and organic groups containing from 1 to about 6 carbon atoms and is only present where X is nitrogen; a is an integer from about 5 to about 20; b is an integer from 1 to about 20; and c and d are integers from 1 to about 20, where the sum of c and d is from about 3 to about 20; and said second component is selected from the group consisting of cyclic lithioamines, dialkyl lithioamines, cyclic aminoalkyllithium compounds, dialkylaminoalkyllithium compounds, cyclic amino side-chain lithium compounds, and cyclic amino side-chain alkyllithium compounds, wherein said step of combining occurs within a solvent selected from the group consisting of polar solvents, non-polar solvents, and mixtures thereof.

2. A method of preparing a polymer, as set forth in claim 1, wherein said monomers are selected from the group consisting of dienes, vinylaromatics, and trienes.

3. A method of preparing a polymer, as set forth in claim 1, further comprising the step of terminating the polymerization with an agent selected from the group consisting of terminating agents, coupling agents, and linking agents.

4. A method of preparing a polymer, as set forth in claim 1, wherein the non-polar solvent is selected from the group consisting of hexane, cyclohexane, and heptane.

5. A method of preparing a polymer, as set forth in claim 1, wherein the respective ratio of the first component to the second component is in the range from about 90:10 to about 50:50.

6. A method of preparing a polymer, as set forth in claim 1, wherein the respective ratio of the first component to the second component is in the range from about 80:20 to about 50:50.

7. A method of preparing a polymer, as set forth in claim 3, wherein the terminating agent contains tin.

8. The method of claim 1, wherein the second component is a dissimilar lithio amine defined by a formula selected from the group consisting of formulas I and II

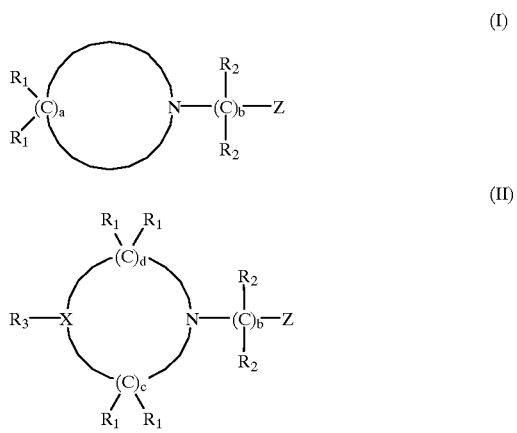

where Z is a lithium atom (Li); where X is a heteroatom selected from the group consisting of sulfur, oxygen and nitrogen; each $R_1$ is independently selected from the group consisting of hydrogen and organic groups containing from 1 to about 12 carbon atoms; each $R_2$ is independently selected from the group consisting of hydrogen and organic groups containing from about 1 to about 4 carbon atoms; $R_3$ is independently selected from the group consisting of hydrogen and organic groups containing from 1 to about 6 carbon atoms and is only present where X is nitrogen; a is an integer from 1 to about 20; b is an integer from 1 to about 20; and c and d are integers from 1 to about 20, where the sum of c and d is from about 3 to about 20.

9. The method of claim 1, wherein the aminoalkyllithium compound defined by the formulas I and II are selected from the group consisting of hexamethyleneiminopropyllithium, hexamethyleneiminohexyllithium, dodecamethyleneiminopropyllithium, 3,3,5-trimethylhexamethylene-imino)propyl lithium, piperidinopropyllithium, and 3-methylpiperidinopropyllithium.

10. The method of claim 9, wherein the aminoalkyllithium is hexamethyleneiminopropyllithium.

11. The method of claim 1, where said step of combining is carried out in an aliphatic solvent.

12. The method of claim 11, wherein said aliphatic solvent is selected from the group consisting of hexane, cyclohexane, and heptane.

* * * * *